United States Patent [19]
Sinofsky

[11] Patent Number: 5,363,387
[45] Date of Patent: Nov. 8, 1994

[54] VARIABLE PULSEWIDTH LASERS

[75] Inventor: Edward L. Sinofsky, Dennis, Mass.

[73] Assignee: Rare Earth Medical, Inc., Dennis, Mass.

[21] Appl. No.: 977,673

[22] Filed: Nov. 18, 1992

[51] Int. Cl.$^5$ .............................................. H01S 3/111
[52] U.S. Cl. ......................................... 372/15; 372/25; 372/99; 372/41; 372/69
[58] Field of Search .................. 372/25, 32, 99, 14–16, 372/41, 69–71, 75, 6

[56] References Cited

U.S. PATENT DOCUMENTS

| | | | |
|---|---|---|---|
| 3,521,069 | 7/1970 | De Maria et al. | 250/199 |
| 3,609,588 | 9/1971 | McKnight | 372/15 |
| 3,611,182 | 10/1971 | Treacy | 372/15 |
| 3,725,817 | 4/1973 | Nolan | 372/16 |
| 3,836,866 | 9/1974 | Ammann et al. | 331/94.5 |
| 4,197,513 | 4/1980 | Bell et al. | 331/94.5 |
| 4,998,259 | 3/1991 | Chandra et al. | 372/15 |
| 5,018,152 | 5/1991 | Linne et al. | 372/25 |
| 5,144,629 | 9/1992 | Basu | 372/20 |
| 5,202,893 | 4/1993 | Kubota et al. | 372/69 |

*Primary Examiner*—Leon Scott, Jr.
*Attorney, Agent, or Firm*—Thomas J. Engellenner

[57] ABSTRACT

A variable pulsewidth laser system is disclosed which employs an oscillating reflector to control the duration of laser pulses. In one embodiment, the oscillating mirror is swept (e.g., caused to swing back and forth) about an axis distinct from the optical axis, such that resonant conditions suitable for laser beam generation occur only at a particular location in the oscillating sweep path. By varying the scanning waveform, laser pulses of different durations can be generated.

21 Claims, 3 Drawing Sheets

SINGLE PULSE PER CYCLE

VARIABLE PULSEWIDTH LASERS

BACKGROUND OF THE INVENTION

The technical field of the invention is Q-switched lasers and, in particular, pulsed lasers having a capacity for adjustable pulse duration independent of repetition rate.

Conventionally, Q-switched lasers employ solid state crystals or other gain media within a cavity to modulate laser resonance. The gain medium stores the energy until a triggering signal or other threshold event causes the energy to be released as a large pulse. For example, the medium or switch can be an acousto-optical or electro-optical crystal which switches the "Q" of the cavity between a high value which supports lasing action within the resonant cavity and a low value which essentially turns off the resonant cavity. While the switch is turned off, the pumping energy builds a population inversion within the cavity. When the Q-switch is turned on, the built-up population inversion is rapidly discharged, resulting in a large pulse of laser energy.

In such conventional Q-switched laser systems, there is typically little or no control over pulsewidth. The pulsewidth is largely dependent on the cavity, itself, and the switching repetition rate. Moreover, conventional Q-switched laser systems are often ill-suited for production of very long laser pulses, e.g., on the order of 10 milliseconds or longer.

There exists a need for variable pulse width lasers, particularly in the medical, communications, and radar fields. Laser surgical systems, in particular, could benefit greatly from a simple laser control system which permitted the user to modify the pulsewidth of therapeutic laser radiation during a surgical procedure. As lasers become more commonplace in medical therapy, it is becoming apparent that different biological structures (e.g., bone and other hard materials versus soft tissue) can be ablated optimally with laser pulses of different peak powers and/or durations. Similarly, non-ablative procedures, such as tissue fusion or suturing, can be performed optimally in yet another pulse mode regime.

Accordingly, a variable pulse width laser system, permitting the operator to modify the pulse widths from about 1 microseconds or less to 10 milliseconds or more, would satisfy a long-felt need in the art.

SUMMARY OF THE INVENTION

It has been discovered that a highly efficient Q-switched laser system can be constructed employing an oscillating reflector to control the duration of laser pulses. In one embodiment, the oscillating mirror is swept (e.g., caused to swing back and forth) about an axis distinct from the optical axis, such that resonant conditions suitable for laser beam generation occur only at a particular location in the oscillating sweep path. By varying the scanning waveform, laser pulses of different durations can be generated.

The oscillating mirror can be controlled, for example, by a scanning galvanometer. The oscillating mirror can be disposed such that it is able to turn about two axes, both of which are substantially orthogonal to the optical axis defined by the resonant cavity. The mirror's position about one of the axes of rotation can be set to insure resonant conditions exist and, by oscillating the mirror about the other axis, an extremely efficient energy extraction of Q-switched pulses is obtained. The oscillating mirror will often be the output mirror.

Pulse widths ranging from about 1.2 microseconds to 24.4 milliseconds have been observed with one experimental prototype. Continuous wave ("CW") laser radiation can also be obtained by maintaining the oscillating mirror in a fixed position. The scanning system of the present invention is robust enough to provide a lifetime of greater than ten million duty cycles.

In another aspect of the invention, techniques and apparatus are disclosed for biasing the scanning means such that resonant conditions occur at a particular point in the scanning process. This is especially useful when the scanning motion is assymetric (i.e., fast in one direction and slower in the other). By triggering resonance at particular times during the oscillating scan of the mirror, pulses of different characteristics can be obtained (e.g., pulse trains consisting of two or more different types of pulses, or maximum single spike energy pulses).

The present invention can be useful in both diode-pumped and lamp-pumped lasers to provide laser systems useful in medicine, or more generally, in material processing. In particular, the invention is especially suited for control of solid state lasers, e.g., diode-pumped rare earth laser systems, such as thulium-doped, yttrium-aluminum garnet (Tm:YAG) crystals, and similar neodymium, erbium or holmium-doped crystals.

In another aspect of the invention, laser surgical instruments based on the oscillating mirror principles are disclosed for use in hand-held surgical tools, endoscopes, catheters and the like. A small rare earth-doped, crystal, such as a Er:YAG or Tm:YAG crystal, is employed as the gain medium. Energy from a laser diode pump source is delivered to the gain medium via one or more optical fibers. The instrument is configured to deliver laser radiation to biological tissue for surgical or other therapeutic purposes.

For example, the invention can be applied to laser dentistry to drill hard tissue (e.g., teeth enamel and bone) using short pulses on the order of about one microsecond to about 100 microseconds with high peak power, to ablate softer tissue (e.g., pulp and necrotic nerves) with longer pulses at lower power, on the order of about 100 microseconds to about 100 milliseconds, and to weld soft tissue or coagulate blood using long pulses (greater than ten milliseconds) or continuous wave radiation at low power.

Efficient production of millisecond-duration laser pulses is particularly desirable in medical therapies in order to minimize acoustic side effects which can be painful and/or damaging to adjacent tissue structures. For example, in laser angioplasty, the acoustic side effects of short laser pulses are often detrimental in that they disrupt or otherwise weaken certain components of the blood vessel walls. Accordingly, a laser angioplasty system capable of generating longer pulses (e.g., greater than 100 microseconds and preferably on the order of one millisecond or greater) is also desired, and can be achieved with the present invention.

Greater efficiency in energy conversion also is achieved with the present invention because of the absence of any intercavity loss-modulating elements which introduce reflective and bulk losses, themselves. Moreover, the present invention has advantages over acousto-optic elements which typically only "hold off" a limited amount of optical power before the gain medium will lase anyway. Similarly, the present invention has advantages over electrooptic switches in which considerable energy is discarded by the polarization process and require very high voltages to achieve switching. Furthermore, the present invention has advantage over prior art rotating polygon systems which control the pulse width by changing the rotational speed of a rotating mirrored-polygonal surface. In such rotating polygon systems, there is little ability to control the repetition rate independent of the pulse width.

By sweeping the mirror element back and forth, rather than employing a rotating polygon, the present invention essentially decouples the pulsewidth from the repetition rate.

The invention will next be described in connection with certain illustrated embodiments; however, it should be clear to those skilled in the art that various changes, additions, subtractions and other modifications can be made without departing from the spirit or scope of the invention. For example, it should be clear that the oscillating mirror need not be the output coupler in all instances (although this will often simplify fabrication and usage). In some applications, the oscillating mirror may be a substantially non-transmissive end or turning mirror, as well.

DETAILED DESCRIPTION

Figure 1:
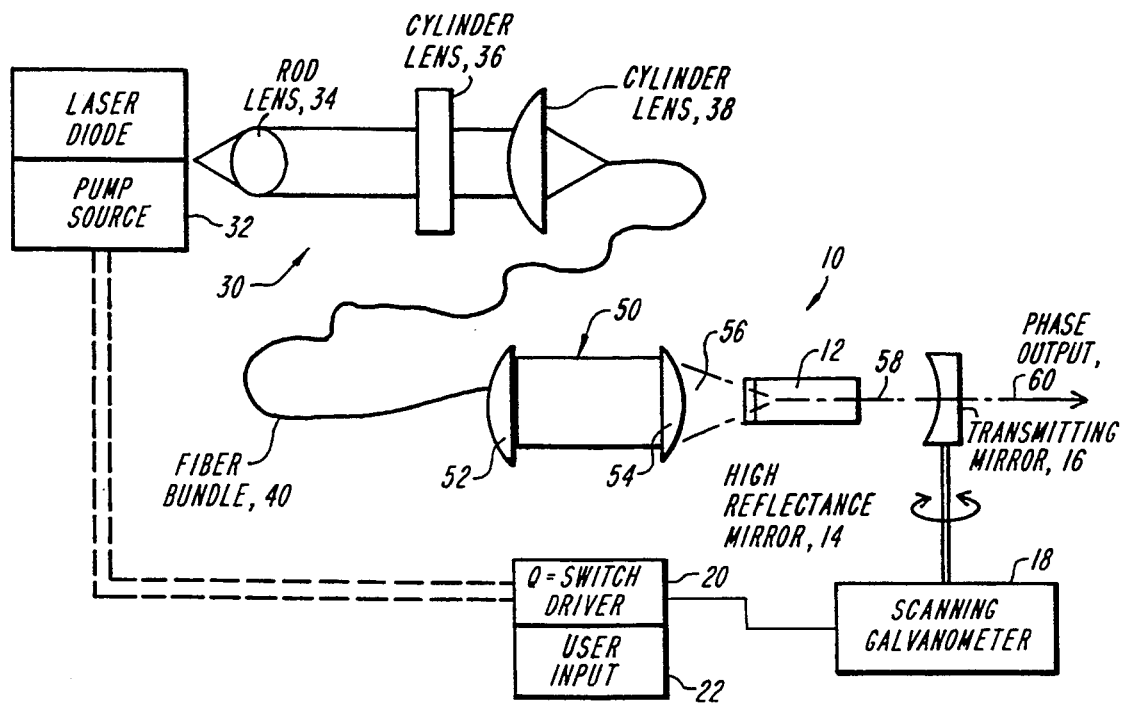
FIG. 1 is a schematic block diagram of a Q-switched laser system according to the present invention.

In FIG. 1, a laser system 10 according to the invention is shown including a gain medium 12 (e.g., a rare earth-doped crystal or the like) disposed within a resonant cavity defined by highly reflective, dichroic mirror 14 and partially-transmitting output mirror 16. In accordance with the present invention, one of the mirrors, preferably the output mirror 16, can be scanned about at least one axis relative to the optical axis. This oscillation of the output mirror 16 can be accomplished by a scanning galvanometer 18 under the control of a Q-switch driver 20 and/or user inputs 22.

As also shown in FIG. 1, The gain medium 12 is preferably pumped by a laser diode pump source 32 which delivers light energy to the gain medium via a fiber bundle 40. At the proximal end of the fiber bundle an optical input coupler 30 is disposed to couple light from the laser diode 32 into the fiber bundle 40. As shown, the optical input coupler 30 includes a rod lens 34, a cylinder lens 36, and a second, orthogonally-disposed, cylinder lens 38. At the distal end of the fiber bundle, a fiber output coupler 50 can be used to deliver the pump radiation through dichroic mirror 14 to the gain medium. As shown, the fiber output coupler 50 includes a first cylinder lens 52 which collimates the radiation exiting the fiber bundle, and a second cylinder lens 54 which focuses the pump radiation 56 into the gain medium.

Figure 2:
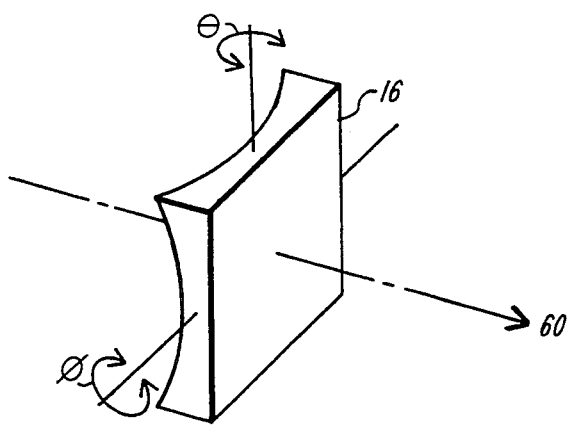
FIG. 2 is more detailed schematic illustration of a partially-transmissive output mirror according to the invention, showing its rotational degrees of freedom.

In FIG. 2 the rotational degrees of freedom of the oscillating mirror 16 are shown relative to the optical axis of the light output 60. As can be seen from FIG. 2, the mirror 16 is free to rotate about two, preferably orthogonal, axes. Oscillation about one axis defines the pulse width and adjustment of the rotational position about the other axis ensures that the mirror is properly aligned to achieve resonance.

Figure 3:
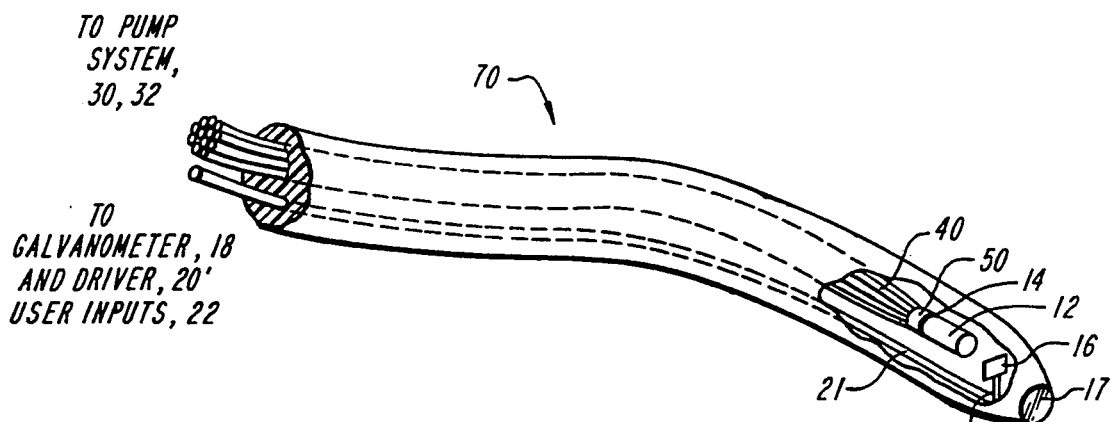
FIG. 3 is a schematic illustration of a surgical tool incorporating a Q-switched laser system according to the present invention.

In FIG. 3, the core structure 70 of a compact, variable-pulsewidth laser system is shown for use in a surgical instrument, such as a hand-held laser scalpel, dental drill, endoscope or catheter. In this embodiment, a fiber bundle 40 delivers pump radiation via coupler 50 to a gain medium 12 disposed within a resonant cavity defined by mirror 14 and mirror 16. Mirror 14 is a highly-reflective, dichroic mirror which provides little or no impedance to the optical pump energy from the fiber bundle 40 but reflects virtually all of the radiation generated by the gain medium upon excitation. Mirror 16 is a partially-transmissive output mirror and is disposed at the distal end of the instrument in a mechanical gimble arrangement or the like such that it may rotate about two axes relative to the optical beam path. Linkage 19 and mechanical cable 21 permit adjustment of the mirror 16 about these two axes. The cable 21 is connected to a galvanometer 18 under control of driver 20 and user inputs 22, as shown and described in connection with FIG. 1. Optical fiber 40 is connected to the pump system 30, 32, as likewise discussed above in description of FIG. 1.

By manipulation of the oscillation rate of mirror 16, laser radiation pulses of a desired duration can be achieved. Such laser radiation is emitted from the distal tip of the instrument and can be, optionally, focused by focusing lens 17 prior to irradiation of a target region of biological tissue.

Figure 4:
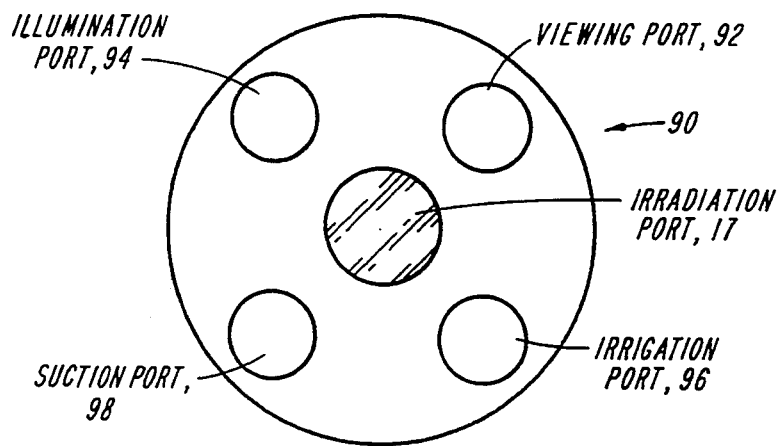
FIG. 4 is a schematic end view of an endoscopic or catheter instrument incorporating a Q-switched laser system according to the present invention.

In FIG. 4, the present invention is further illustrated within the context of an endoscopic or catheter instrument. FIG. 4 is an end view of the distal end of such an instrument which can incorporate the structure described above in connection with FIG. 3. As shown, the variable pulse width laser radiation can be emitted from the irradiation port 17 of FIG. 4 while various other functionalities can also be incorporated into the endoscopic catheter instrument 90 including, for example, a viewing port 92, an illumination port 94, an irrigation port 96, and a suction port 98.

Another aspect of the invention, namely the location of resonant conditions within the scanning cycle of the oscillating mirror, is illustrated by the timing diagrams of FIGS. 5-9.

Figure 5:
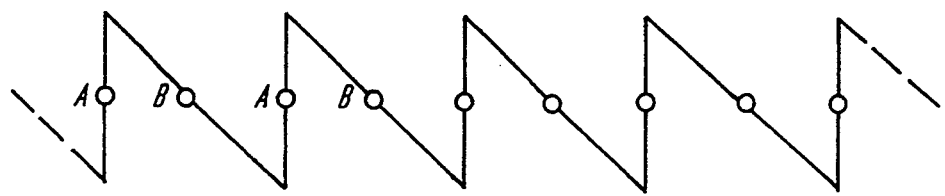
FIG. 5 is a timing diagram illustrating the operation of the present invention.

In FIG. 5, a basic "saw-tooth" or triangular waveform is depicted illustrating the scanning action of a conventional galvanometer, available from General Scanning Co., Watertown, Mass. The sloped line indicates the scanning action of the mirror while the vertical line represents the "fly-back" operation for returning the mirror to its original position. In operation, a pulse is triggered during both the scanning and fly-back operations as shown in FIG. 5. It should be appreciated, though, that the pulse generated during fly-back operation (schematically illustrated as pulse "A") will be of shorter duration than the pulse "B" generated during scanning operation. The pulses illustrated in FIG. 5 have a uniform repetition rate.

Figure 6:
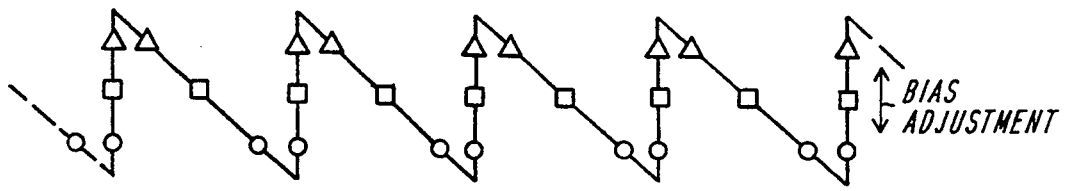
FIG. 6 is a timing diagram illustrating the effects of scanner bias adjustment on operation of the present invention.

As shown in FIG. 6, the DC bias applied to the scanner can be varied to produce pulses of adjustable timing and different energies.

Figure 7:
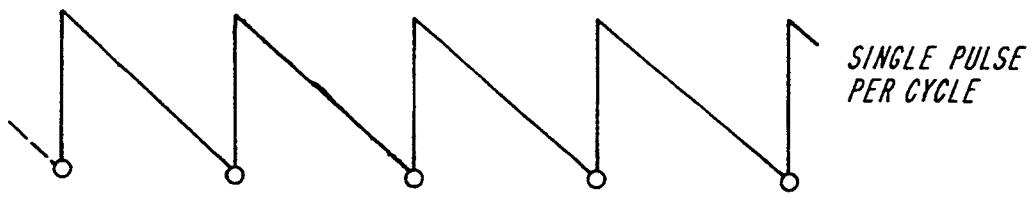
FIG. 7 is a timing diagram illustrating a bias setting that yield a single pulse per cycle in the operation of the present invention.

In FIG. 7, the bias of the scanning action is set to generate a single spike pulse at the very end of a scanning sweep. This results in a single pulse per cycle.

Figure 8:
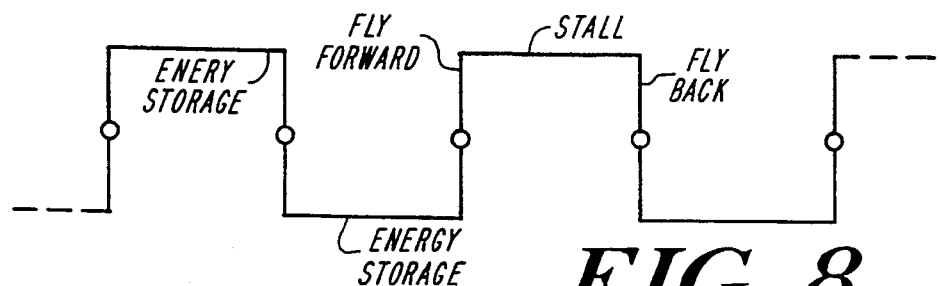
FIG. 8 is a timing diagram illustrating another mode of operation in the present invention yielding very rapid pulses.

In FIG. 8, an alternative scanning action is illustrated for the production of very short pulses in which the oscillating mirror is driven with a square wave function in which energy is accumulated in the gain medium during a "stall" condition depicted by the horizontal lines, and pulses are generated during "fly-forward" and "fly-back" operations as illustrated by the vertical lines in the figure.

Figure 9:
FIG. 9 is a timing diagram illustrating yet another mode of operation in the present invention yielding very long pulses.

On the other hand, longer pulses can be achieved using a low amplitude sinusoidal function as illustrated schematically in FIG. 9.

The pulsewidth of laser pulses according to the present invention can be further refined by coordination of the pump energy impulses with the scanning action of the oscillating mirror. For example, if the pump source is a pulsed source, the pulses can be triggered to precede or coincide with the sweep of the oscillating mirror to a location that switches on the laser action. In such a procedure, laser energy extraction can often be maximized.

What is claimed is:

1. In a laser apparatus having a resonant cavity with an optical axis defined by a high reflection mirror and a transmitting mirror, a gain medium disposed between said mirrors, and a pump source for generating a population inversion within said medium and thereby inducing radiation to traverse said cavity along an optical path between said mirrors, the improvement comprising:

sweeping means for scanning one of said mirrors in a back and forth motion about an axis distinct the optical axis, such that an output of laser radiation occurs in a pulse at a discrete time and for a discrete duration, the pulse duration being proportional to the rate of back and forth motion of the swept mirror, and the sweeping means further comprising means for varying the angular velocity of said swept mirror.

2. The apparatus of claim 1 wherein the apparatus further comprises waveforming means for applying a defined waveform to said sweeping means to modify said pulse duration.

3. The apparatus of claim 1 wherein the apparatus further comprises a driver which activates the pump source in coordination with the motion of the oscillating mirror.

4. The apparatus of claim 3 wherein the driver further comprises means for adjusting said motion to select a pulse initiation time.

5. The apparatus of claim 1 wherein the pump source is an optical pump source which delivers radiation to said gain medium.

6. The apparatus of claim 5 wherein the apparatus further comprises at least one optical fiber disposed between said pump source and said gain medium for delivering said radiation from the pump source to the gain medium.

7. The apparatus of claim 1 wherein tile pump source is a laser diode.

8. The apparatus of claim 1 wherein the sweeping means further comprises means for varying the angular extent of said motion during scanning.

9. The apparatus of claim 1 wherein the transmitting mirror is rotatable about at least two different axes, each of which is distinct from the optical axis.

10. The apparatus of claim 1 wherein gain medium is a rare earth-doped crystal.

11. The apparatus claim 10 wherein the crystal chosen from the group consisting of thulium-doped crystals, erbium-doped crystals, holmium-doped crystals and neodymium-doped crystals.

12. A method of producing laser radiation pulses defined pulsewidth comprising:

disposing a gain medium within a resonant cavity having an optical axis, said resonant cavity being defined by a high reflection mirror and a transmitting mirror;

energizing said gain medium with energy from a pump source to generate a population inversion within said medium and thereby induce radiation to traverse said cavity along an optical path between said mirrors; and scanning one of said mirrors in a back and forth sweeping motion about an axis distinct from the optical axis, such that an output of laser radiation occurs in a pulse at a discrete time and for a discrete duration when the mirrors are positioned to support lasing activity within said cavity, the pulse duration being proportional to the rate of back and forth motion of the swept mirror, and the sweeping means further comprising means for varying the angular velocity of said swept mirror.

13. The method of claim 12 wherein the method further comprises applying a defined waveform to a sweeping means to modify the rate of said motion and, thereby, modify said pulse duration.

14. The method of claim 13 wherein the method further comprises adjusting the angular extent of scanning motion.

15. The method of claim 13 wherein the method further comprises delivering radiation to said gain medium.

16. The method of claim 15 wherein the method further comprises employing at least on optical fiber to deliver said radiation from the pump source to the gain medium.

17. The method of claim 12 wherein the method further comprises activating said pump source with the sweep or said oscillating mirror.

18. The method of claim 12 wherein the step of oscillating the position of the oscillating mirror further comprises driving a sweeping means with a periodic ramp function.

19. The method of claim 12 wherein the step of oscillating the position of the oscillating mirror further comprises driving a sweeping means with a periodic square-wave function.

20. The method of claim 12 wherein the step of oscillating the position of the oscillating mirror further comprises driving a sweeping means with a periodic, sinusoidal function.

21. A laser instrument comprises:
   a housing;
   a highly reflective mirror and a partially transmissive mirror disposed within said housing, which mirrors define a resonant cavity;
   a rare earth-doped crystal gain medium disposed in said housing between said mirrors or said resonant cavity;
   a pump source delivery means for delivering energy to said gain medium; and
   sweeping means also disposed within said cavity for varying the orientation of one of said mirrors relative to the optical axis by scanning one of said mirrors in a back and forth motion about an axis distinct the optical axis, such that an output of laser radiation occurs in a pulse of a predefined time and for a predefined duration, the pulse duration being proportional to the rate of back and forth motion of the swept mirror, and the sweeping means further comprising means for varying the angular velocity of said swept mirror.

* * * * *